US009358072B2

(12) United States Patent
Ullrich (10) Patent No.: US 9,358,072 B2
(45) Date of Patent: Jun. 7, 2016

(54) SYSTEMS AND METHODS FOR MINIMALLY INVASIVE SURGICAL TOOLS WITH HAPTIC FEEDBACK (75) Inventor: Christopher J. Ullrich, Ventura, CA (US)

(73) Assignee: Immersion Corporation, San Jose, CA (US)

(*) Notice: Subject to any disclaimer, the term of this patent is extended or adjusted under 35 U.S.C. 154(b) by 481 days.

(21) Appl. No.: 13/007,251

(22) Filed: Jan. 14, 2011

(65) Prior Publication Data
US 2011/0178508 A1 Jul. 21, 2011

Related U.S. Application Data (60) Provisional application No. 61/295,438, filed on Jan. 15, 2010.

(51) Int. Cl.
| | |
|---|---|
| *A61M 25/01* | (2006.01) |
| *A61B 19/00* | (2006.01) |
| *A61B 17/00* | (2006.01) |
| *A61B 5/00* | (2006.01) |
| *A61B 5/0205* | (2006.01) |
| *A61B 5/042* | (2006.01) |

(52) U.S. Cl.
CPC ............ *A61B 19/22* (2013.01); *A61B 17/00234* (2013.01); *A61M 25/01* (2013.01); *A61B 5/0084* (2013.01); *A61B 5/0205* (2013.01); *A61B 5/042* (2013.01); *A61B 19/2203* (2013.01); *A61B 2019/2211* (2013.01); *A61B 2019/2292* (2013.01); *A61B 2019/2296* (2013.01); *A61B 2019/465* (2013.01); *A61M 25/0113* (2013.01); *A61M 25/0116* (2013.01)

(58) Field of Classification Search
None
See application file for complete search history.

(56) References Cited

U.S. PATENT DOCUMENTS

| 5,080,104 A | * | 1/1992 | Marks et al. .................. 600/461 |
| 5,320,608 A | * | 6/1994 | Gerrone ............ A61B 17/3417 604/117 |
| 5,339,799 A | | 8/1994 | Kami et al. |
| 5,389,849 A | | 2/1995 | Asano et al. |

(Continued)

FOREIGN PATENT DOCUMENTS

| CA | 2 520 942 | 3/2007 |
| DE | 42 13 426 A1 | 10/1992 |

(Continued)

OTHER PUBLICATIONS

The Macmillan Encyclopedia, Electrocardiography, Market House Books Ltd 2003.*

(Continued)

*Primary Examiner* — Lynsey Crandall
*Assistant Examiner* — Manolis Pahakis
(74) *Attorney, Agent, or Firm* — Kilpatrick Townsend & Stockton LLP (57) ABSTRACT Systems and methods for minimally invasive surgical tools with haptic feedback are disclosed. One disclosed embodiment of a system includes an insertion sheath configured to be partially inserted within a patient's body, the insertion sheath configured to receive a surgical tool; a roller disposed at least partially within the insertion sheath, the roller configured to contact a surgical tool inserted within the insertion sheath; and an actuator coupled to the roller, the actuator configured to receive an actuator signal and to output a haptic effect based on the actuator signal.

24 Claims, 8 Drawing Sheets (56) References Cited

U.S. PATENT DOCUMENTS

| | | | |
|---|---|---|---|
| 5,431,645 A * | 7/1995 | Smith et al. | 606/1 |
| 5,480,422 A * | 1/1996 | Ben-Haim | 607/122 |
| 5,540,681 A * | 7/1996 | Strul et al. | 606/34 |
| 5,667,517 A * | 9/1997 | Hooven | 606/151 |
| 5,720,742 A * | 2/1998 | Zacharias | 606/1 |
| 5,728,044 A * | 3/1998 | Shan | A61B 1/31 33/512 |
| 5,755,668 A | 5/1998 | Itoigawa et al. | |
| 5,805,140 A * | 9/1998 | Rosenberg et al. | 345/161 |
| 5,810,841 A * | 9/1998 | McNeirney et al. | 606/130 |
| 5,821,920 A * | 10/1998 | Rosenberg et al. | 345/156 |
| 5,833,634 A | 11/1998 | Laird et al. | |
| 5,853,392 A * | 12/1998 | Dennis | 604/164.01 |
| 5,929,846 A * | 7/1999 | Rosenberg et al. | 345/161 |
| 6,088,020 A * | 7/2000 | Mor | B25J 13/02 318/628 |
| 6,096,004 A * | 8/2000 | Meglan | A61B 19/22 604/95.01 |
| 6,154,201 A * | 11/2000 | Levin et al. | 345/184 |
| 6,171,234 B1 | 1/2001 | White et al. | |
| 6,184,868 B1 * | 2/2001 | Shahoian et al. | 345/161 |
| 6,224,586 B1 | 5/2001 | Stephens | |
| 6,373,465 B2 * | 4/2002 | Jolly et al. | 345/156 |
| 6,377,011 B1 * | 4/2002 | Ben-Ur | 318/566 |
| 6,470,302 B1 * | 10/2002 | Cunningham et al. | 703/7 |
| 6,612,992 B1 * | 9/2003 | Hossack | A61B 5/06 600/467 |
| 6,697,044 B2 * | 2/2004 | Shahoian et al. | 345/156 |
| 6,717,573 B1 * | 4/2004 | Shahoian et al. | 345/161 |
| 6,726,675 B1 * | 4/2004 | Beyar | 604/510 |
| 6,776,765 B2 * | 8/2004 | Soukup et al. | 600/585 |
| 6,817,973 B2 * | 11/2004 | Merril et al. | 600/118 |
| 6,834,647 B2 * | 12/2004 | Blair et al. | 128/204.18 |
| 6,929,481 B1 | 8/2005 | Alexander et al. | 434/262 |
| 7,056,123 B2 * | 6/2006 | Gregorio et al. | 434/272 |
| 7,196,688 B2 * | 3/2007 | Schena | 345/156 |
| 7,198,137 B2 * | 4/2007 | Olien | 188/1.11 E |
| 7,289,106 B2 * | 10/2007 | Bailey et al. | 345/158 |
| 7,300,450 B2 | 11/2007 | Vleugels et al. | |
| 7,344,507 B2 * | 3/2008 | Briggs et al. | 600/583 |
| 7,344,533 B2 * | 3/2008 | Pearson et al. | 606/41 |
| 7,522,152 B2 * | 4/2009 | Olien et al. | 345/156 |
| 7,570,254 B2 * | 8/2009 | Suzuki et al. | 345/184 |
| 7,669,598 B2 * | 3/2010 | Rick et al. | 128/204.21 |
| 7,815,436 B2 * | 10/2010 | Cunningham et al. | 434/262 |
| 7,819,799 B2 * | 10/2010 | Merril et al. | 600/118 |
| 7,877,243 B2 * | 1/2011 | Olien et al. | 703/3 |
| 7,963,925 B1 * | 6/2011 | Schecter | 600/508 |
| 7,972,141 B2 * | 7/2011 | Morris | 434/268 |
| 8,002,089 B2 * | 8/2011 | Jasso et al. | 188/83 |
| 8,043,229 B2 * | 10/2011 | Mulvihill et al. | 600/568 |
| 8,128,622 B2 * | 3/2012 | Podhajsky et al. | 606/47 |
| 8,187,229 B2 * | 5/2012 | Weitzner et al. | 604/158 |
| 8,221,308 B2 * | 7/2012 | Noguchi et al. | 600/117 |
| 8,292,831 B2 * | 10/2012 | Fausett | A61B 5/1114 600/587 |
| 8,328,738 B2 * | 12/2012 | Frankhouser et al. | 600/587 |
| 8,715,271 B2 | 5/2014 | Fujimoto et al. | |
| 8,942,828 B1 * | 1/2015 | Schecter | 607/122 |
| 8,998,890 B2 * | 4/2015 | Paul | A61N 1/40 600/547 |
| 2001/0025150 A1 * | 9/2001 | de Juan, Jr. | A61B 5/6848 600/587 |
| 2002/0120188 A1 * | 8/2002 | Brock et al. | 600/407 |
| 2003/0187343 A1 * | 10/2003 | Cuzzani | A61B 3/16 600/399 |
| 2004/0106916 A1 * | 6/2004 | Quaid | A61B 19/2203 606/1 |
| 2004/0167559 A1 | 8/2004 | Taylor et al. | |
| 2004/0210186 A1 * | 10/2004 | Arnett et al. | 604/35 |
| 2005/0021078 A1 * | 1/2005 | Vleugels | A61B 17/29 606/205 |
| 2005/0214723 A1 * | 9/2005 | Feygin et al. | 434/262 |
| 2005/0245910 A1 * | 11/2005 | Wright | A61F 9/00745 606/1 |
| 2006/0041245 A1 | 2/2006 | Ferry et al. | |
| 2006/0142657 A1 | 6/2006 | Quaid et al. | |
| 2006/0146010 A1 * | 7/2006 | Schneider | 345/156 |
| 2006/0161045 A1 | 7/2006 | Merril et al. | |
| 2007/0004984 A1 * | 1/2007 | Crum et al. | 600/471 |
| 2007/0018958 A1 * | 1/2007 | Tavakoli | A61B 19/2203 345/161 |
| 2007/0063971 A1 * | 3/2007 | Vecerina et al. | 345/156 |
| 2007/0103437 A1 * | 5/2007 | Rosenberg | 345/161 |
| 2007/0129626 A1 * | 6/2007 | Mahesh et al. | 600/407 |
| 2007/0135735 A1 * | 6/2007 | Ellis | A61B 5/11 600/587 |
| 2007/0142749 A1 * | 6/2007 | Khatib | A61B 6/12 600/587 |
| 2007/0149931 A1 * | 6/2007 | Cannon et al. | 604/264 |
| 2007/0152974 A1 * | 7/2007 | Kim et al. | 345/168 |
| 2007/0197939 A1 * | 8/2007 | Wallace et al. | 600/587 |
| 2007/0233044 A1 | 10/2007 | Wallace | |
| 2007/0299304 A1 | 12/2007 | Murakami et al. | |
| 2008/0009791 A1 | 1/2008 | Cohen et al. | |
| 2008/0221439 A1 * | 9/2008 | Iddan et al. | 600/424 |
| 2008/0228104 A1 * | 9/2008 | Uber et al. | 600/567 |
| 2008/0249395 A1 * | 10/2008 | Shachar et al. | 600/409 |
| 2008/0275442 A1 | 11/2008 | Paul et al. | |
| 2008/0275465 A1 * | 11/2008 | Paul et al. | 606/129 |
| 2008/0297287 A1 * | 12/2008 | Shachar et al. | 335/234 |
| 2008/0319279 A1 * | 12/2008 | Ramsay et al. | 600/301 |
| 2009/0030332 A1 * | 1/2009 | Schecter | 600/508 |
| 2009/0062686 A1 * | 3/2009 | Hyde et al. | 600/558 |
| 2009/0156921 A1 * | 6/2009 | Wang | 600/364 |
| 2009/0158852 A1 | 6/2009 | Paul et al. | |
| 2009/0234273 A1 * | 9/2009 | Intoccia | A61B 17/3417 604/22 |
| 2009/0248042 A1 * | 10/2009 | Kirschenman | A61B 19/2203 606/130 |
| 2009/0281478 A1 * | 11/2009 | Duke | 604/22 |
| 2009/0306547 A1 * | 12/2009 | Iddan et al. | 600/585 |
| 2010/0057099 A1 * | 3/2010 | Fujimoto et al. | 606/130 |
| 2010/0073150 A1 * | 3/2010 | Olson | A61B 19/2203 340/407.1 |
| 2010/0095961 A1 * | 4/2010 | Tornesel et al. | 128/203.12 |
| 2010/0152586 A1 * | 6/2010 | Grant | A61B 5/489 600/454 |
| 2010/0161022 A1 * | 6/2010 | Tolkowsky | 623/1.11 |
| 2010/0168572 A1 * | 7/2010 | Sliwa | A61B 8/0833 600/439 |
| 2010/0178644 A1 * | 7/2010 | Meglan et al. | 434/267 |
| 2010/0249796 A1 * | 9/2010 | Nycz | A61B 19/5244 606/99 |
| 2010/0312129 A1 * | 12/2010 | Schecter | A61B 5/0031 600/508 |
| 2011/0015569 A1 * | 1/2011 | Kirschenman | A61B 17/2909 604/95.01 |
| 2011/0046659 A1 | 2/2011 | Ramstein et al. | |
| 2011/0152882 A1 * | 6/2011 | Wenderow et al. | 606/130 |
| 2011/0152901 A1 * | 6/2011 | Woodruff | A61F 5/0056 606/157 |
| 2011/0319815 A1 * | 12/2011 | Roelle | A61B 1/00149 604/95.01 |
| 2012/0041436 A1 * | 2/2012 | Ullrich | A61B 18/12 606/39 |
| 2013/0274712 A1 * | 10/2013 | Schecter | A61M 25/10 604/510 |

FOREIGN PATENT DOCUMENTS

| | | |
|---|---|---|
| EP | 1 108 394 A2 | 6/2001 |
| JP | 2006-325916 | 12/2006 |
| WO | WO 03/020139 A2 | 3/2003 |
| WO | WO 2004/067053 A2 | 8/2004 |
| WO | WO 2005/013803 A2 | 2/2005 |
| WO | WO 2006091494 A1 * | 8/2006 |
| WO | WO 2006120666 A1 * | 11/2006 |
| WO | WO 2007/051000 | 5/2007 |

(56) References Cited

FOREIGN PATENT DOCUMENTS

| WO | WO 2008/085919 | 7/2008 | |
|---|---|---|---|
| WO | WO 2009009220 A2 * | 1/2009 | A61B 17/00 |

OTHER PUBLICATIONS

Patent Cooperation Treaty, International Search Report and Written Opinion, Application No. PCT/US2011/021349, mailed Jun. 16, 2011.

Patent Cooperation Treaty, International Search Report, International Application No. PCT/US2008/063561, dated Jan. 30, 2009.

European Patent Office, Communication pursuant to Article 94(3) EPC, European Application No. 11703519, dated Mar. 5, 2014.

Japanese Patent Office, Office Action, Application No. 2012-549125, dated Sep. 16, 2014.

Patent Cooperation Treaty, Preliminary Report on Patentability, International Application No. PCT/US2011/021349, dated Jul. 26, 2012.

* cited by examiner

SYSTEMS AND METHODS FOR MINIMALLY INVASIVE SURGICAL TOOLS WITH HAPTIC FEEDBACK

CROSS-REFERENCES TO RELATED APPLICATION

This application claims priority to U.S. Provisional Patent Application No. 61/295,438 filed Jan. 15, 2010, entitled Minimally Invasive Surgical Tools with Haptic Feedback, the entirety of which is hereby incorporated by reference.

FIELD OF THE INVENTION

The present invention generally relates to surgical tools and more specifically to systems and methods for medical simulation and more particularly to systems and methods for minimally invasive surgical tools with haptic feedback.

BACKGROUND

Minimally invasive surgery is performed without making a major incision or opening, resulting in reduced trauma for the patient and yielding significant cost savings. These result from shorter hospitalization times and reduced therapy requirements. Other benefits of minimally invasive surgery include less pain, less need for post-surgical pain medication, less scarring, and less likelihood of complications related to the incision.

Minimally invasive surgery is defined either as based on the operative procedure (e.g., small incisions) or the outcome (e.g., reduced surgical complications or costs). However, minimally invasive surgery is not the same as minor surgery. Some "minimally invasive" procedures, e.g., coronary artery bypass surgery, still are major operations requiring a hospital stay.

In minimally invasive surgery, a miniature camera is typically introduced into the body through a small incision. The camera transmits images to a video monitor, enabling the physician to diagnose and, if necessary, treat a variety of conditions. To do this, the physician inserts surgical instruments and auxiliary devices (collectively, "minimally invasive surgical tools"), such as irrigation and drainage devices, through one or more additional small incisions. Such surgical instruments can be for laparoscopic surgery, catheterization or endoscopy, as well as for enabling telesurgery and telepresence. Compared to open surgery, however, minimally invasive surgery presents limitations in visual and haptic perceptions, and creates challenges unique to this type of surgery. One of the major concerns is the potential for tissue damage, possibly caused by inappropriate use of force.

SUMMARY

Embodiments of the present invention provide systems and methods for minimally invasive surgical tools with haptic feedback. For example, in one embodiment, a system includes an insertion sheath configured to be partially inserted within a patient's body, the insertion sheath configured to receive a surgical tool; a roller disposed at least partially within the insertion sheath, the roller configured to contact a surgical tool inserted within the insertion sheath; and an actuator coupled to the roller, the actuator configured to receive an actuator signal and to output a haptic effect based on the actuator signal.

In one embodiment of a method, the method comprises a computer-implemented method, comprising receiving a sensor signal from a sensor coupled to a surgical tool, the surgical tool configured to be at least partially inserted within a patient's body; generating an actuator signal based at least in part on the sensor signal, the actuator signal configured to cause the actuator to output a haptic effect; and transmitting the actuator signal to an actuator coupled to the surgical tool. In another embodiment, a computer-readable medium comprises program code for causing a processor to execute such a method These illustrative embodiments are mentioned not to limit or define the invention, but rather to provide examples to aid understanding thereof. Illustrative embodiments are discussed in the Detailed Description, which provides further description of the invention. Advantages offered by various embodiments of this invention may be further understood by examining this specification.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

DETAILED DESCRIPTION

Example embodiments are described herein in the context of systems and methods for minimally invasive surgical tools with haptic feedback. Those of ordinary skill in the art will realize that the following description is illustrative only and is not intended to be in any way limiting. Other embodiments will readily suggest themselves to such skilled persons having the benefit of this disclosure. Reference will now be made in detail to implementations of example embodiments as illustrated in the accompanying drawings. The same reference indicators will be used throughout the drawings and the following description to refer to the same or like items.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Further, in the disclosed embodiments below, the term "or" may be used to describe different features of particular embodiments. Use of the term "or" is intended to be interpreted both as inclusive and exclusive, thus combinations may include any or all of the identified features as described herein.

Illustrative System for Minimally Invasive Surgical Tools with Haptic Feedback

In one illustrative system for minimally invasive surgical tools with haptic feedback, the system is configured to assist a surgeon during minimally invasive surgery (MIS) on a live patient. For example, a surgeon may perform a MIS to perform cardio electrophysiology to measure changes in electric potentials (i.e. voltages) on the inside surface of a patient's heart, such as following a heart attack, to detect any abnormalities or to ablate heart tissue to address arrhythmias.

Figure 1:
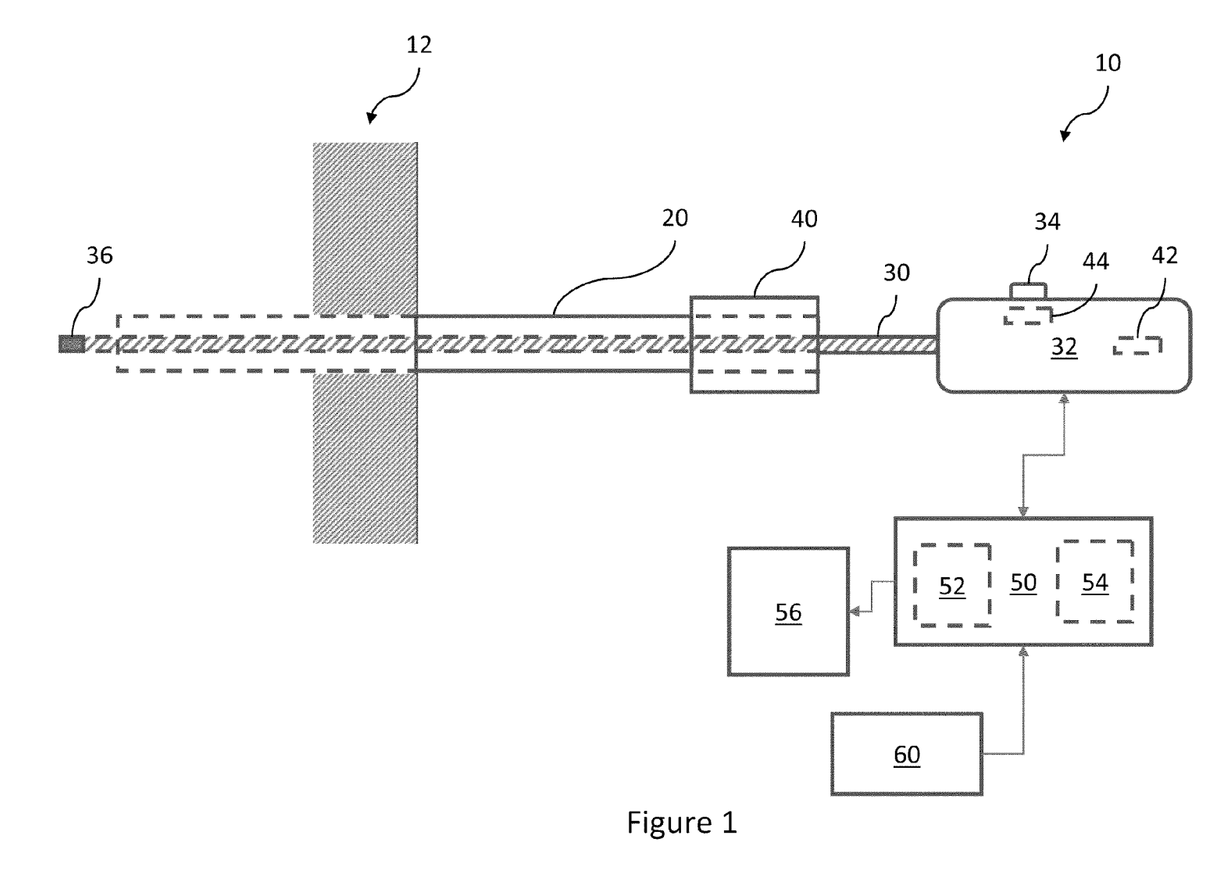
FIG. 1 shows an illustrative system for minimally invasive surgical tools with haptic feedback according to one embodiment of the present invention.

Referring now to FIG. 1, FIG. 1 shows an illustrative embodiment of a system 10 for minimally invasive surgical tools with haptic feedback according to one embodiment of the present invention. The system 10 in FIG. 1 comprises an insertion sheath 20, a surgical tool 30 (a guide wire, in this case) with a handle 32, a computer 50 with a processor 52, memory 54 and a display 56, and a heart rate monitor 60.

To perform the illustrative MIS procedure, the surgeon makes an incision in the patient's leg 12 and inserts an insertion sheath 20, in this case a catheter, into the patient's femoral artery to provide an insertion path for a surgical tool. The surgeon then inserts the catheter 20 through the patient's vascular system until it reaches the patient's heart. The surgeon may then insert a surgical tool 30, such as a guide wire equipped with a voltage sensor 36 or sensors on the distal end of the guide wire 30 through the catheter 20 to the patient's heart to measure voltages at various points on or within the heart's walls. Such a guide wire 30 typically has a proximal end that is connected to a handle 32 to allow the surgeon to maneuver the guide wire 30 to reach various points on interest on the heart's wall. To maneuver the guide wire 30, the surgeon manipulates one or more manipulanda 34, e.g. knobs or levers, on the guide wire's handle 32 to move the distal tip of the guide wire 30 in any of a number of directions. In such an embodiment, the surgeon may then maneuver the guide wire's distal tip to contact the heart's wall to take voltage measurements with the sensor(s) 36.

In the illustrative embodiment shown in FIG. 1, the insertion tube 30 has been equipped with an actuator 40 to assist the surgeon in performing the MIS procedure. An inductive actuator 40 configured in a ring or cylindrical shape has been coupled to the proximal end of the insertion tube 20 such that the guide wire 30 passes through the actuator 40 into the insertion tube 30. The inductive actuator 40 can be actuated by transmitting an electrical current through the coils of the actuator 40 to generate electromagnetic forces on the guide wire 30 to provide kinesthetic haptic effects to assist or resist translational movement of the guide wire 30 within the insertion tube. An advantage of using an inductive actuator may be that, because there is no physical coupling between the actuator and the guide wire as there might be when using a roller, a surgeon manipulating the guide wire may receive more accurate tactile sensations because there is no friction and inertia to overcome as may be the case were rollers or other frictional contact employed. However, other types of actuators may be employed as will be discussed in more detail below.

In addition, the handle 32 of the guide wire 30 includes a plurality of actuators 42, 44. One of the actuators 42 is a vibrotactile actuator and is used to output vibrational effects to the guide wire handle 32 based on the voltages sensed by the sensor(s) 36 on the distal end of the guide wire. For example, the frequency of a vibration effect may be proportional to the magnitude of the voltage sensed by the sensor(s) 36, thus providing the surgeon with additional information regarding the status of the procedure. The vibrational information in this case is in addition to a display showing graphical information about the various sensor readings.

The second actuator 44 disposed within the handle 32 is configured to provide haptic effects to the manipulandum 34 on the handle. For example, the second actuator 44 may output haptic effects based on a contact force between the distal tip of the guide wire and the wall of the heart, or based on an angle of attack of the distal tip of the guide wire and the wall of the heart. In the embodiment shown, the second actuator 44 outputs a kinesthetic force to resist movement of the manipulandum 34 based on a sensed force on the tip of the distal end of the guide wire (force sensor not shown).

The computer 50, which comprises a processor 52 and a memory 54, receives sensor signals from the surgical tool 30 and, in some instances, the insertion sheath 20, and generates actuator signals to cause haptic effects to be output by the various actuators 40, 42, 44 on the guide wire 30, the guide wire handle 32 or manipulandum 34. In addition, the computer 50 receives information from other external devices, such as the heart monitor 60, which it may use as well to generate haptic effects. Examples of other external sensors include heart rate monitors, blood pressure monitors, oxygen sensors, blood gas sensors, etc.

For example, in this illustrative embodiment, heart rate monitor 60 is connected to the patient and provides heart rate information to the computer 50. The computer 50 can generate haptic effects to indicate if the patient's heart rate falls outside of acceptable limits. Because the surgeon may be focused on the particular voltage readings and manipulating the guide wire, this additional information may not be immediately apparent to the surgeon. For example, if the patient's heart begins beating too rapidly, the computer 50 can generate an actuator signal to cause a haptic effect to indicate a potentially dangerous condition and bring the abnormal heart rate to the surgeon's attention.

In addition, the computer 50 can output display signals to cause the display 56 to display relevant information to the surgeon, such as visual indications of sensed voltages, images from a camera inserted into the catheter, heart rate, etc. Thus, the system 10 can provide an immersive, integrated experience that allows the surgeon to focus on the MIS procedure, while receiving a variety of inputs that provide immediate tactile responses to the surgeon to allow her to better perform the procedure and monitor conditions that might otherwise divert her attention.

Figure 2A:
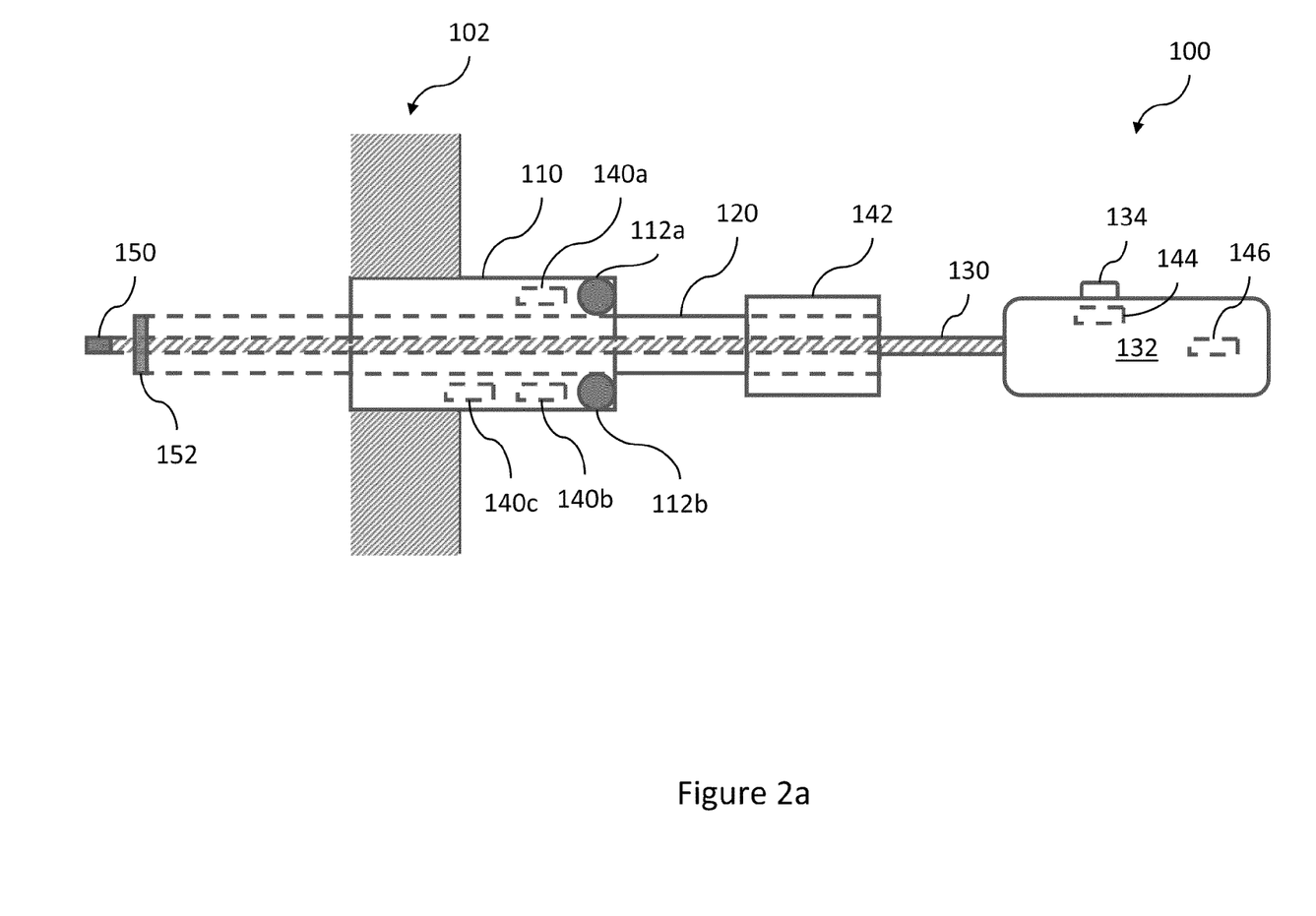
FIGS. 2-3 show systems for minimally invasive surgical tools with haptic feedback according to embodiments of the present invention.

Referring now to FIG. 2a, FIG. 2a shows a system 100 for minimally invasive surgical tools according to one embodiment of the present invention. System 100 comprises an insertion sheath 110, a first surgical tool 120, and a second surgical tool 130. Insertion sheath 110 comprises a plurality of rollers 112a,b and a plurality of actuators 140a,b, each coupled to one of the plurality of rollers 112a,b. Insertion sheath 110 is configured to be partially inserted into the patient's body 102 and to receive a surgical tool, such as surgical tool 120. In the embodiment shown, the insertion sheath 110 comprises a trocar.

In the embodiment shown, rollers 112a,b are configured to contact surgical tool 120 and are configured to output haptic forces created by the actuation of actuators 140a,b, respectively. In one embodiment, each of actuators 140a,b is an active actuator and is configured to cause its respective roller 112a,b to rotate. By rotating the respective rollers, actuators 140a,b can output kinesthetic forces configured to assist or resist translational movement of surgical tool 120 within the insertion sheath 110. For example, in the embodiment shown, actuators 140a,b comprise DC motors but could also include passive actuators (i.e. magnetic brakes), cams or other friction producing or modulating means. In some embodiments, however, actuators 140a,b comprise passive actuators configured to brake their respective roller 112a,b to resist translational movement of the surgical tool 120 within the insertion sheath 110. In some embodiments, one or both rollers 112a,b are coupled to sensors, such as rotational encoders, that are configured to detect a rotation of the roller 112a,b. In one such embodiment, the sensors are configured to transmit a sensor signal to a processor to indicate a movement or position of the roller based on a corresponding movement of the surgical tool 120.

In some embodiments, the trocar 110 is configured to be sterilized between MIS procedures, though in some embodiments, trocar 110 is configured to be discarded. Because rollers 112a,b are configured to contact surgical tool 120, they are either configured to be discarded or sterilized between MIS procedures. In some embodiments, rollers 112a,b and actuators 140a,b may be disposed within a subassembly that is configured to be releasably coupled to the insertion sheath 110 such that the insertion sheath 110 and the roller/actuator subassembly can be decoupled following a MIS procedure and each can be individually sterilized or discarded.

In addition to actuators 140a,b, insertion sheath 110 also comprises vibrotactile actuator 140c, which is configured to apply vibrotactile haptic effects to the surgical tool 120 or the insertion sheath 110. In the embodiment shown, actuator 140c comprises a piezoelectric actuator, though in other embodiments, other types of actuators may be employed, such as eccentric rotating masses, linear resonant actuators, voice coils, or other suitable actuators. In addition, a plurality of vibrotactile actuators may be incorporated into the sheath, or, in some embodiments, no vibrotactile actuators may be employed.

In the embodiment shown, surgical tool 120 comprises a catheter and thus may be both a surgical tool and an insertion sheath. Surgical tool 120 is configured to be inserted into insertion sheath 110 and to be inserted into a patient's body 102. In the embodiment shown, surgical tool 120 comprises at least one sensor 152 coupled to the distal end of the surgical tool. The sensor 152 comprises a force sensor and is configured to sense a contact force between the distal end of the surgical tool 120 and an obstacle, such as a stenosis or an internal organ. The sensor 152 is configured to generate a sensor signal indicating a magnitude of the sensed force and to transmit the sensor signal to a processor (not shown), which may use the sensor signal to actuate one or more actuators 140a,b coupled to the insertion sheath. For example, the actuators may generate a force to resist further insertion of the surgical tool, such as to amplify a sensed force on a distal tip of the surgical tool 120. In some embodiments, the processor may generate a signal to cause the actuators 140a,b to completely resist or prevent further insertion of the surgical tool 120, or to reverse the motion of the surgical tool to withdraw the surgical tool 120. One such embodiment may be advantageous as it may prevent a surgeon from inadvertently puncturing an internal organ or a blood vessel within a patient.

In some embodiments, other types of sensors 152 may be affixed to the distal tip of the surgical tool 120, such as voltage sensors, temperature sensors, fluid flow sensors, or viscosity sensors. In some embodiments, one or more sensors may be affixed to other portions of the surgical tool 120 or inserted into the surgical tool 120. For example, a sensor (or sensors) may be inserted into surgical tool 120, such as a fiber optic sensor, fluoroscope, or video camera to provide sensor signals to a processor. In some embodiments, one or more sensors may be arrayed within the surgical tool 120, such as to sense a position of a further surgical tool 130 inserted within surgical tool 120 or the amount of bend within a surgical tool. For example, in some MIS procedures, a surgeon may navigate through a tortuous portion of the vascular system, such as in a patient's brain, and may need an indication of much the surgical tool is bending during performance of the procedure. If too much bending is sensed, a processor may generate a haptic effect based on the sensed amount of bend and output a haptic effect to the surgical tool or handle. In some embodiments, a system 100 may comprise non-colocated sensors configured to detect a distance between the sensors, a change in resistance or voltage between the sensors, or other differences is status between the two sensors to generate a sensor signal. In one such an embodiment, the distal end of a surgical tool 120, 130 may comprise a first sensor and the insertion sheath 110,120 may comprise a second sensor. A processor may detect a difference in sensor readings between the two sensors and generate an actuator signal based on the difference. In one embodiment, the sensors may be configured to detect a distance between the sensors and generate one or more sensor signals and transmit the sensor signals to a processor.

Surgical tool 120 may also comprise an actuator 142 coupled to the surgical tool 120. In the embodiment shown, the actuator 142 is releasably coupled to the surgical tool 120, though in some embodiments the actuator 142 may be permanently coupled to, or integrally disposed within, the surgical tool. In this embodiment, actuator 142 comprises an inductive actuator and is configured to provide haptic effects to surgical tools, such as surgical tool 130, that have been inserted within surgical tool 120. As discussed above, surgical tool 120 comprises a catheter and thus is configured to allow one or more surgical tools to be inserted within surgical tool 120. For example, in the embodiment shown in FIG. 2a, surgical tool 130 comprises a guide wire and is configured to be inserted within catheter 120. In such an embodiment, actuator 142 is configured to generate electromagnetic forces to resist or assist translational movement of the guide wire 130 within the catheter. In other embodiments, surgical tool 130 may comprise other suitable surgical tools, such as a deflectable catheter or an electrophysiology probe. As discussed above, inductive actuators may provide advantages in such MIS procedures because they do not require a surgeon to overcome friction or inertia of a roller or other physical coupling to move guide wire 130 within surgical tool 120. However, in some embodiments, other types of actuators may be used, such as one or more rollers.

Figure 2B:
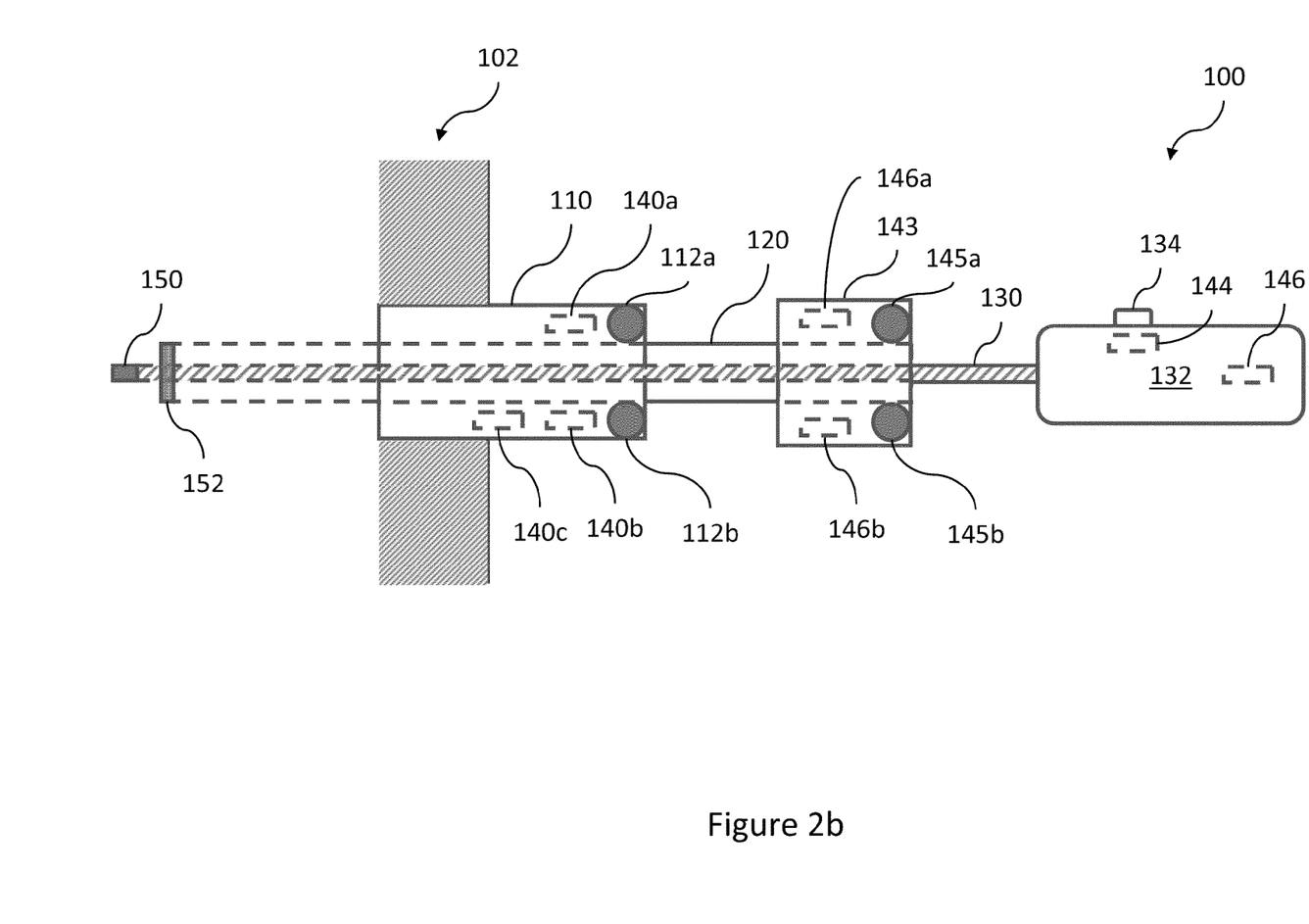

For example, FIG. 2b shows a system for minimally invasive surgical tools with haptic feedback in which surgical tool 120 is coupled to an actuator 143 which comprises a plurality of rollers 145a,b at least partially disposed within actuator 143. Each roller 145a,b is in communication with an actuator 146a,b, which are configured to impart forces on surgical tool 130 by rotating rollers 145a,b or resisting rotation of roller 145a,b, thereby assisting or resisting translational movement of surgical tool 130 within surgical tool 120. As discussed above with respect to insertion sheath 110, actuators 145a,b may comprise active or passive actuators, or in some embodiments, may comprise one of each or a plurality of different types of actuators. Actuator 143 may be desirable in embodiments in which surgical tool 130 may be adversely affected by the use of an inductive actuator 142 or surgical tool 130 is not susceptible to forces generated by an inductive actuator 142. Further, as discussed above, actuators 142, 143 may be used to assist with the insertion of a surgical tool 130 within surgical tool 120 or to resist movement or prevent movement if surgical tool 130 may puncture a patient's organ or blood vessel.

Figure 2C:
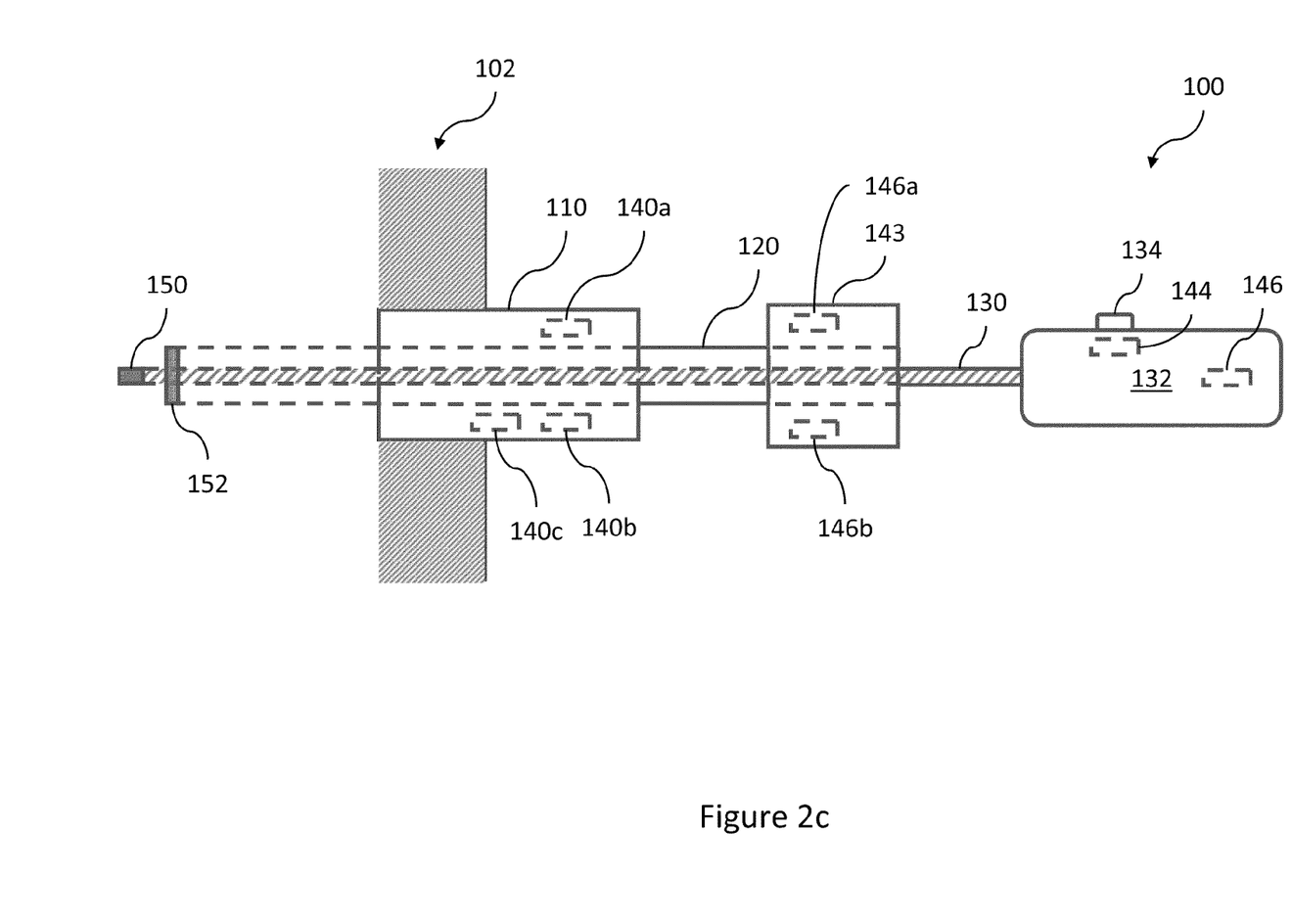

Referring now to FIG. 2c, FIG. 2c shows a system for minimally invasive surgical tools with haptic feedback according to one embodiment of the present invention. The embodiment shown in FIG. 2c is similar to those shown in FIGS. 2a and 2b, however, the insertion sheath 110 comprises actuators 140a-c but does not include the rollers 112a,b. Instead, actuators 140a-c are configured to output haptic effects to the insertion sheath 110 or to the surgical tool 120. For example, in one embodiment, one or more of actuators 140a-c comprise vibrotactile actuators, such as eccentric rotating masses. In one embodiment, one or more of actuators 140a-c comprise resistive actuators configured to resist movement of the surgical tool 120. For example, in one embodiment, actuators 140a,b each comprise a braking surface configured to be moved into contact with the surgical tool 120 to apply a resistive force on the surgical tool. In one embodiment, one or more of actuators 140a-c may comprise an inductive actuator configured to exert a force on the surgical tool. In a further embodiment, one or more of actuators 140a-c may be configured to alter the surface friction of the surgical tool to create a resistance to movement of the surgical tool within its insertion sheath or delivery catheter. Thus, while some embodiments shown and discussed herein employ one or more rollers to apply forces to surgical tool 120, other embodiments may be configured to only vibrotactile forces on the insertion sheath 110 or to apply forces to the surgical tool 120 using other mechanisms.

Referring again to FIG. 2a, in the embodiment shown, surgical tool 130 is configured to be inserted within surgical tool 120 and comprises at least one sensor 150 coupled to the surgical tool's 130 distal tip. The proximal end of surgical tool 130 is coupled to a handle 132, which is configured to allow a surgeon or other user to insert or retract the surgical tool 130 within surgical tool 120. In addition, handle 132 comprises one or more manipulanda 134 to manipulate the distal tip of the surgical tool 130. For example, manipulandum 134 may be used to bend the distal tip of the surgical tool 130 away from the longitudinal axis of the surgical tool 130, thereby "steering" the surgical tool in a particular direction. In addition, handle 132 comprises a plurality of actuators configured to output haptic effects to a user of the handle 132.

In the embodiment shown, handle 132 is releasably coupled to surgical tool 130. As previously discussed, MIS surgical tools typically must be sterilized or discarded after being used in an MIS procedure. Thus, in one embodiment handle 132 is configured to be decoupled from surgical tool 132 and discarded after use in an MIS procedure. In another embodiment, handle 132 is configured to be sterilized following an MIS procedure. Further, in some embodiments, handle 132 is permanently coupled to surgical tool 130 and thus may be discarded with surgical tool 130 or sterilized with surgical tool 130.

Actuator 146 comprises a vibrotactile actuator configured to output a vibrational or vibrotactile effect to the handle 132. For example, in the embodiment shown, actuator 146 comprises an eccentric rotating mass (ERM) coupled to a rotary motor. In some embodiments, other types of actuators may be employed, such as piezoelectric actuators, voice coils, or linear resonant actuators (LRAs). In some embodiments, a plurality of vibrotactile actuators may be disposed within the handle 132, while in other embodiments, no vibrotactile actuators may be used.

The vibrotactile actuator 146 may be employed to provide information associated with the MIS procedure to a surgeon or user of the handle 132. For example, in the illustrative embodiment discussed previously, the distal tip of a surgical tool 130 may be coupled to a voltage sensor 150 which provides sensor signals to a processor indicating sensed voltages on a patient's heart. The processor may then generate actuator signals to cause the vibrotactile actuator 146 to output a vibration to the handle 132 based at least in part on the sensed voltage. In one embodiment, the distal tip of the surgical tool 130 may also, or instead, be fitted with a force sensor 150 which provides a sensor signal comprising force information to the processor, which generates actuator signals to generate vibrational haptic effects proportional in magnitude to the force sensed by the sensor 150. Such an embodiment may provide additional information to a surgeon beyond the information provided by other actuators in the system 100, such as actuator 142 or 143.

While actuators 142, 143 may resist movement of the surgical tool, vibrational effects provided by actuators 146 may provide an indication of the magnitude of the force applied by the tool on an obstacle that may be useful in combination with resistances generated by other actuators 142, 143. Still further information may be output by actuator 146. For example, external sensors may transmit sensor signals to a processor, which may generate actuator signals to actuator 146 to cause it to output a vibrational effect to the handle 132 to apprise a surgeon of another condition that is not related to forces or sensor readings from the surgical tool. For example, external sensors may include heart monitors, blood pressure monitors, blood oxygen monitors, or other sensors monitoring a patient's status.

In addition to, or instead of, vibrotactile actuator 146, handle 132 may comprise actuator 144, which is configured to output kinesthetic forces to manipulandum 134. In the embodiment shown, the actuator is configured to output a force to resist or assist the movement of manipulandum 134. For example, a processor in communication with the surgical tool 130 may detect that further movement of the distal tip of surgical tool 130 is applying too much pressure to a patient's blood vessel or internal organ and a generate an actuator signal to cause the actuator 144 to resist movement of the manipulandum 134. In one embodiment, surgical tool 130 may comprise a sensor 150 that detects an angle of attack of the distal tip of the surgical tool as it approaches or contacts an obstruction within a patient. For example, if an angle of attack of the distal tip is too shallow, a second sensor coupled to the tip of the surgical tool 130 may be unable to accurately sense a condition within a patient, or, in a procedure where a puncture must be made (e.g. a trans-septal puncture), if the angle of attack is too shallow, the tool may puncture the organ and exit the organ in the wrong location. In such an embodiment, the actuator 144 may output a force to prevent further movement of the manipulandum 134. In addition, actuator 142, 143 may output a force to prevent further insertion of the surgical tool 130. In some embodiments, actuator 144 may be configured to output a vibrational effect, such as to indicate that the angle of attack is too shallow or that a dangerous amount of pressure is being exerted by the distal tip of the surgical tool 130, rather than a resistive force.

Figure 3:
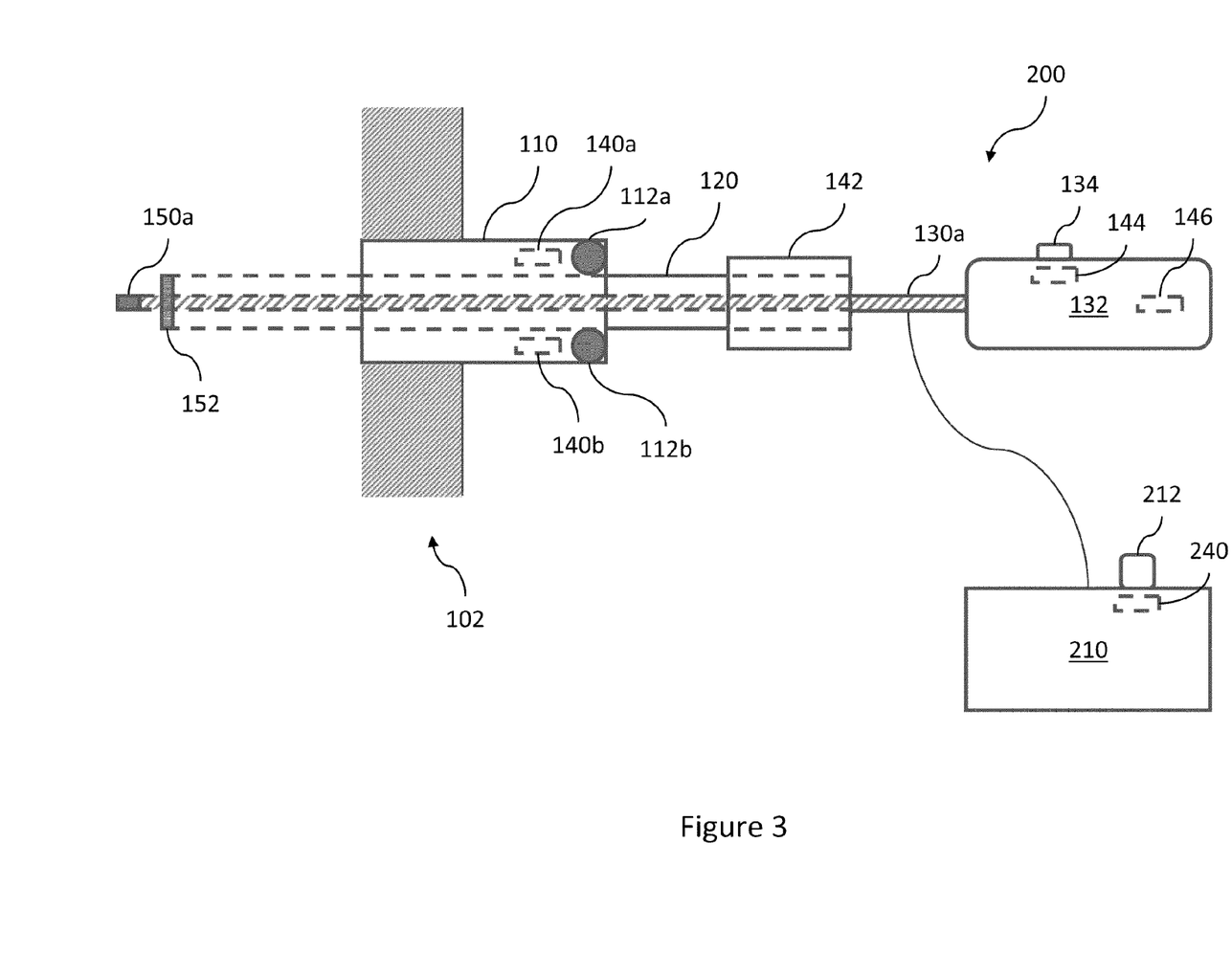

Referring now to FIG. 3, FIG. 3 shows a system 200 for minimally invasive surgical tools with haptic feedback according to one embodiment of the present invention. The system 200 shown in FIG. 3 comprises the embodiment shown in FIG. 2a coupled to a power supply 210 and trigger 212 for a therapeutic surgical tool 130a. In the embodiment shown in FIG. 3, surgical tool 130a comprises an ablation tool 150a coupled to the distal tip of the surgical tool 130a in addition to sensor(s) 150. The ablation tool 150a is configured to receive power signals from the power supply 210 and to ablate tissue contacted by the ablation tool 150.

Power supply 210 comprises a trigger 212 and an actuator 240 and is configured to supply power signals, such as electric current or electric voltage, to the surgical tool 130a and ablation tool 150a. The trigger 212 is used by an operator, such as a surgeon, to apply power to the ablation tool 150a and may comprise a pressure sensitive switch, a slider control, a knob, an on/off switch, or other trigger mechanism. In one embodiment, as more pressure is applied to the trigger 212, more power may be transmitted to the ablation tool 150a. Actuator 240 is configured to output a force to the trigger 212 to provide feedback to the operator to indicate whether too much power is applied or whether too much tissue may have been ablated. For example, in one embodiment, actuator 240 comprises an electromagnetic actuator configured to output a force to resist depression of the trigger 212. As tissue is ablated, a processor (not shown) may determine the quantity of tissue ablated based on a sensor or calculations made using pre-defined characteristics of a patient. The processor may then generate actuator signals and transmit the actuator signals to cause the electromagnetic actuator to resist depression of the trigger 212 and may cause the trigger to be opened to reduce or halt the flow of power to the ablation tool 150a. Further, a second actuator (not shown) may be in communication with the trigger 212 to output a vibrotactile effect to the trigger 212 to indicate a warning to the operator in addition to the resistance generated by the first actuator 240. Such an indication may be advantageous as it may provide confirmation to the surgeon of an error condition rather than just a sticky power trigger. In a further embodiment, actuator 146 may be actuated to output a vibrational effect as tissue is ablated. In still a further embodiment, actuator 144 may be an actuator to resist further movement of the distal tip of the surgical tool 130a towards additional tissue within the patient, thus providing multiple channels of haptic input to the operator: resistance to the trigger 212, vibrational effects on the trigger 212, vibrational effects on the handle 132 and resistance to movement of the distal tip of the surgical tool 130a. Such varied haptic effects may provide more meaningful feedback to a surgeon and help prevent inadvertent injury to a patient.

Figure 4A:
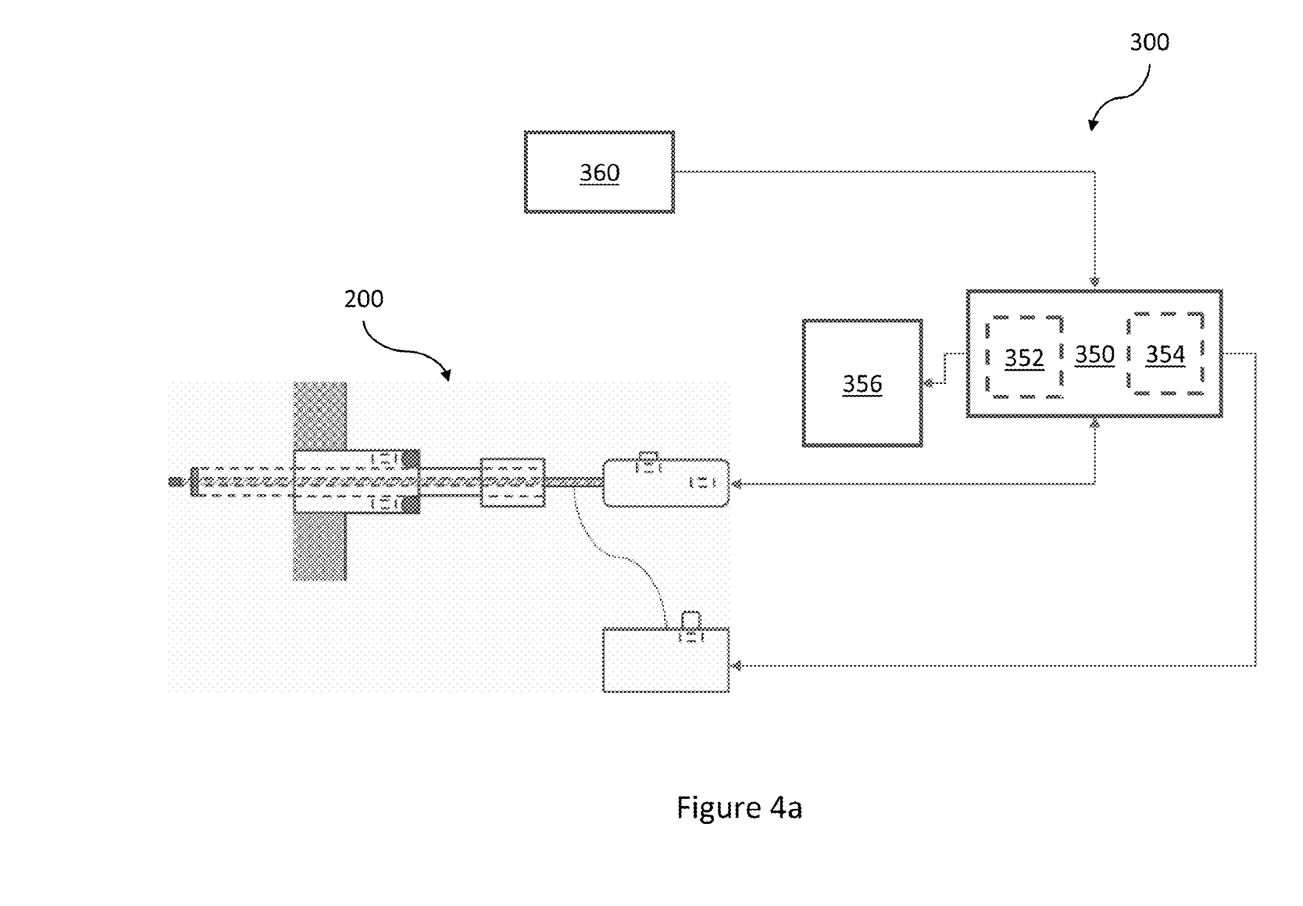
FIGS. 4a-b show systems for minimally invasive surgical tools with haptic feedback according to embodiments of the present invention.

Referring now to FIG. 4a, FIG. 4a shows a system 300 for minimally invasive surgical tools with haptic feedback according to embodiments of the present invention. In the embodiment shown in FIG. 4a, the system 300 comprises the system 200 shown in FIG. 3 in communication with a computer 350 comprising a processor 352 and a memory 354. The system 300 further comprises an external sensor 360 in communication with the computer 350. Computer 350 is configured to receive sensor signals from the various sensors 150, 152 located within system 200 and to generate actuator signals to be transmitted to one or more of the actuators (e.g. 140a-c, 142, 144, 146, 240) in the system 200. In addition, computer 350 is configured to generate and transmit display signals to display 356 to provide information to a surgeon or other operator of the system 300.

Figure 4B:
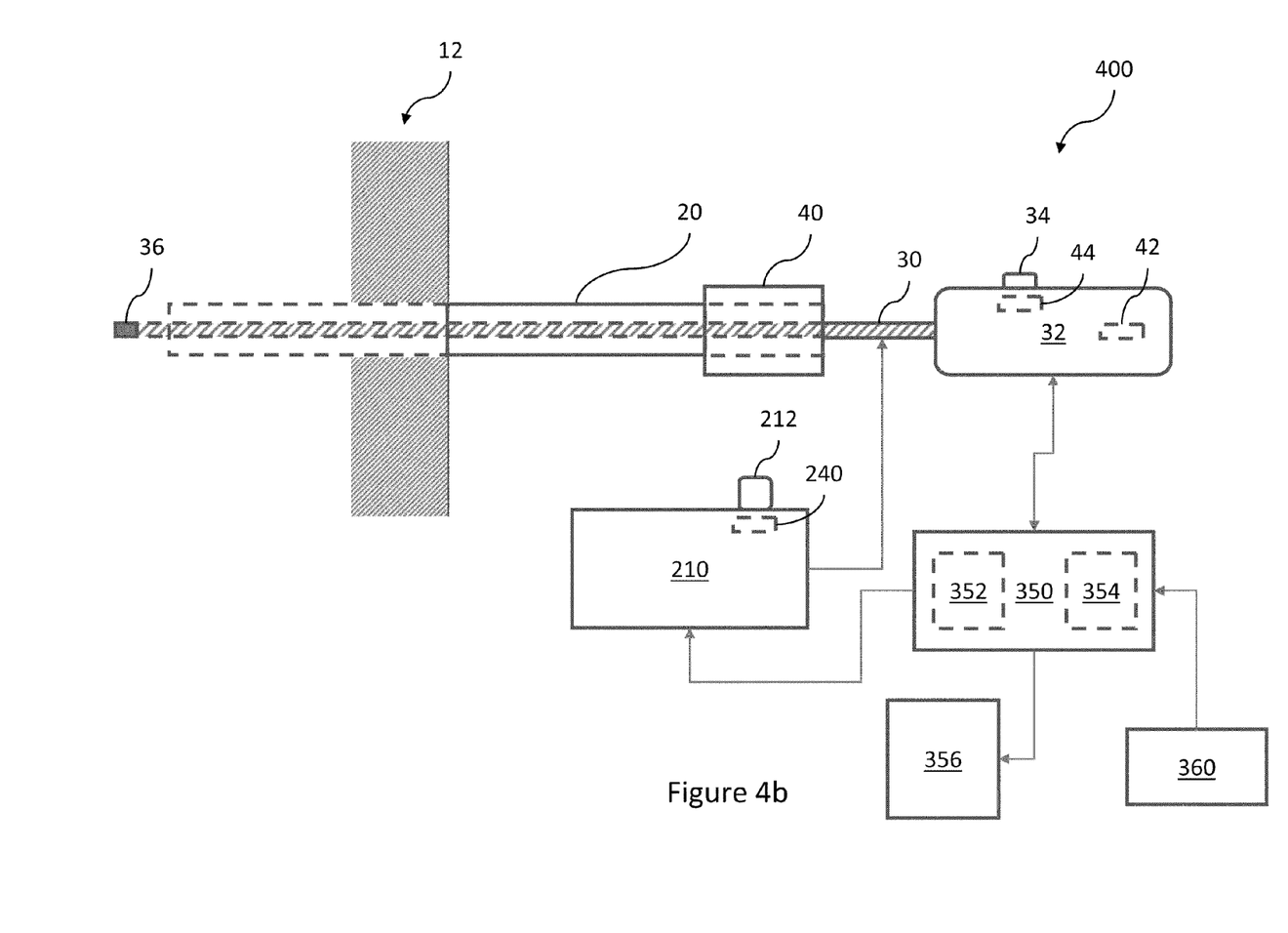

Note that while the embodiment shown in FIG. 4a comprises the system 200 shown in FIG. 3, other systems according to some embodiments of the present invention may be coupled to the computer 350, such as those shown in any of FIGS. 1-3. FIG. 4b shows one such alternate embodiment in which a system 400 comprises a system having components arranged as shown in FIG. 1, as well as a power supply 210 with a manipulandum 212 and an actuator 240 as shown in FIG. 3.

Processor 352 is configured to execute program code stored in a computer-readable medium to receive sensor information and to generate haptic effects associated with the MIS procedure being performed. Embodiments of various types of processors and computer-readable media are disclosed below. Reference is made now to the method 500 shown in FIG. 5, which, in one embodiment, is implemented by programming code stored in memory 354 and executed by the processor 352 shown in FIGS. 4a-b.

Figure 5:
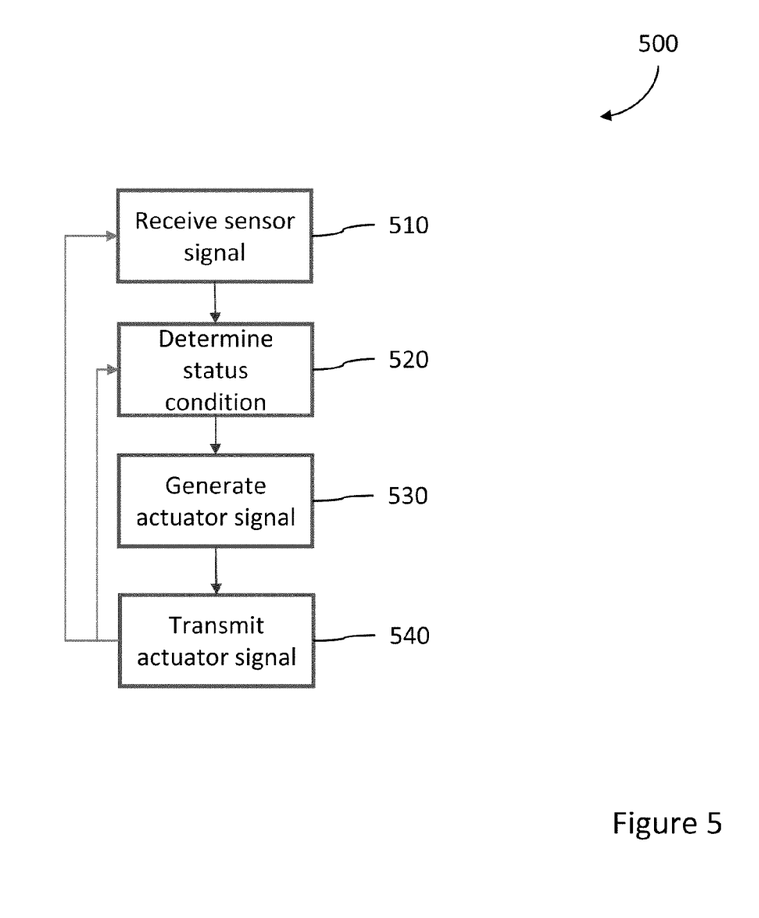
FIG. 5 shows a method for minimally invasive surgical tools with haptic feedback according to one embodiment of the present invention.

In the embodiment shown in FIG. 5, the method 500 begins at block 510 where the processor 352 receives a sensor signal from a sensor, such as sensor 150. In the embodiment shown, sensor 150 comprises a sensor configured to detect an angle of attack of the distal tip of surgical tool 130a when it contacts an obstacle. The sensor signal comprises information associated with the sensed angle of attack. In one embodiment, the processor 352 may receive a plurality of sensor signals from one or more sensors. For example, surgical tool 130a may comprise a plurality of sensors, such as an angle of attack sensor and a force sensor such that the processor 352 receives a sensor signal from each of the sensors, or receives multiple sensor signals from one or more of the sensors.

Other sensors within the system 200 may also transmit sensor signals to the processor. For example, sensor 152 on the distal end of the catheter may transmit a sensor signal that is received by the processor. In addition, as discussed previously, rollers 112a,b may be coupled to, or may comprise, rotational encoders that sense a rotation or position of the rollers 112a,b and transmit a sensor signal to the processor indicating the position or movement of the rollers 112a,b. Processor 352 then receives such sensor signals. Additionally, as shown in FIG. 4a, computer 350 is configured to receive signals from external sensor 360, which comprises a heart rate monitor in the embodiment shown. After receiving a sensor signal, the method 500 proceeds to block 520.

At block 520, the processor 352 determines a status condition associated with the received sensor signal. For example, if the processor 352 receives a sensor signal from a force sensor, the processor 352 may determine a force associated with the sensor signal and compare the force with a threshold. For example, the processor 352 may determine that a force exceeds a first pre-determined threshold and thus a minor danger exists of puncturing tissue within the patient. Or the processor 352 may determine that the force exceeds a higher threshold and thus a serious or critical danger exists of puncturing tissue within the patient. In one embodiment for performing an ablation procedure, it may be desirable to maintain a relatively constant pressure between the ablation tool 150a and a patient's tissue. In such an embodiment, the processor 352 may apply an assistive force to increase a force between the ablation tool 150a and the tissue if the sensed pressure falls below a lower threshold or apply a resistive force, or withdraw the surgical tool 130a, if the pressure exceeds an upper threshold of sensed force.

In another embodiment, the processor 352 may receive a sensor signal indicating a voltage on the surface of an internal organ. The processor may then compare the voltage to one or more voltage thresholds. Alternatively, the processor 352 may simply store the voltage for later use. Still other types of sensors may result in different types of sensor signals to be received by the processor 352, such as fluid flows, viscosities, pressures, or temperatures associated with conditions present within the patient. Other sensors, such as positional sensors or other sensors located within the insertion sheath or surgical tool (e.g. a catheter) may also transmit sensor signals that are received by the processor 352.

For example, in one embodiment, catheter 120 may comprise a sensor 152 that is configured to detect when a surgical tool 130a has reached the distal end of the catheter 120. In such an embodiment, the processor 352 may receive a sensor signal from the sensor 152 when the surgical tool 130*a* reaches the sensor 152 and the processor 352 determines that the surgical tool 130*a* has been fully inserted into the catheter. Alternatively, the processor 352 may receive a sensor signal from the sensor 150 indicating that the surgical tool 130*a* has not reached the distal end of the catheter. In such an embodiment, the processor 352 may be controlling an actuator, such as actuator 143, to automatically insert the surgical tool 130*a* into the catheter 120. Thus, the processor 352 determines that the surgical tool has not yet reached the distal end of the catheter. After determining a status condition associated with the sensor signal, the method proceeds to block 530.

At block 530, the processor 352 generates an actuator signal based at least in part on the sensor signal or the status condition. For example, as discussed above, the processor 352 determined a status condition associated with a sensed force between the surgical tool 130*a* and an obstacle. In such an embodiment, the processor 352 generates an actuator signal configured to increase a resistance to movement of the surgical tool such that the rolling resistance of the rollers 112*a,b* may be varied to provide an amplification of the actual force being applied by surgical tool 130 to allow increased precision. For example, the processor 352 may generate an actuator signal to be transmitted to actuator 142 or 143 to generate a force opposing further movement of the surgical tool 130*a* into surgical tool 120. In a related embodiment, if the processor 352 has determined that a dangerous amount of pressure is being applied, the processor 352 may generate an actuator signal configured to prevent further movement of the surgical tool 130*a* into surgical tool 120 or to reverse movement of the surgical tool 130*a* and to withdraw the surgical tool 130*a* until the sensed force falls below a threshold. Such an embodiment may be advantageous as it may prevent inadvertent injury to a patient.

In a related embodiment, the processor 352 may receive a sensor signal indicating a status associated with manipulandum 134 or power supply 210. For example, in one embodiment, the surgical tool may comprise a manipulandum configured to control the surgical tool. In such an embodiment, the surgical tool 130 or other part of the system 200 may comprise sensors that provide sensor signals associated with the manipulation of the surgical tool, such as force sensors, angle of attack sensors, etc. Processor 352 may receive such sensor signals and generate actuator signals configured to cause an actuator, such as actuator 144, to apply a haptic effect to the manipulandum, such as to assist or resist movement of the manipulandum or to provide a vibrotactile effect to the manipulandum 134.

For example, as discussed above, during an ablation process, once the distal tip of the surgical tool 130*a* is in place, the actuated rollers 112*a,b* could be used to generate an actuator signal to ensure a required force on the tissue is maintained. The actuator signal can be configured to force the distal tip of the surgical tool 130 into contact with the tissue within a pre-determined range such as by either applying pressure in addition to pressure applied by the surgeon or by resisting further pressure or retracting to surgical tool 130*a*. A similar control method could also be utilized in a trans-septal puncture. Once the surgical tool 130 is in place to perform the puncture, the actuated rollers 112*a,b* could be used to perform a very controlled puncture using a controlled level of pressure to cause the puncture.

In one embodiment, the processor 352 may generate an actuator signal based on a non-tactile sensed condition. For example, a sensor may be configured to sense conditions that are not forces, such as voltages, etc. In such an embodiment, the processor 352 may generate a haptic effect based on such a sensed condition. In one embodiment, a surgeon performs a MIS procedure to measure voltages occurring on a patient's heart. In such an embodiment, the processor 352 may generate an actuator signal based at least in part on a magnitude of a sensed voltage, a fluctuation of a sensed voltage, or whether the voltage is above or below a threshold. In one such embodiment, the processor may generate an actuator signal to cause an actuator to output a vibrotactile effect. For example, the processor 352 may generate an actuator signal to cause actuator 146 to output a vibrotactile effect based at least in part on a sensed voltage such that the frequency or magnitude of the vibrational effect is proportional to the magnitude of the voltage. Thus, for a relatively high voltage, the processor 352 may generate an actuator signal having a relatively high frequency. Conversely, for a relatively low voltage, the processor 352 may generate an actuator signal having a relatively low frequency.

In a further embodiment, processor 352 may generate an actuator signal based on sensor information or a status condition determined from an external sensor 360. For example, the processor 352 may receive a measured heart rate or blood pressure from the external sensor 360 and determine that the heart rate has fallen below a threshold. In one embodiment, the processor 352 generates an actuator signal configured to cause an actuator 146 to output a vibrotactile effect to the handle 132 of the surgical tool 130, wherein the vibrotactile effect is configured to indicate a warning condition associated with the external sensor. For example, the actuator signal may be configured to cause an actuator, e.g. actuator 146, output a series of pulsed vibrations to simulate a heartbeat to indicate a warning condition associated with the patient's heart rate or blood pressure. In such an embodiment, the magnitude of the vibrations may be proportional to the amount the sensed condition exceeds the threshold. After generating an actuator signal, the method 500 proceeds to block 540

In block 540, the processor 352 transmits the generated actuator signal to an actuator. For example, if the processor 352 has generated an actuator signal to cause a vibrotactile effect to the handle 132 of the surgical tool, the processor 352 transmits the actuator signal to actuator 146. In some embodiments the processor 352 may transmit the actuator signal to a plurality of actuators, or may modify an actuator signal before transmitting the actuator signal. For example, in one embodiment, the processor 352 generates an actuator signal configured to cause actuators 140*a,b* to rotate rollers 112*a,b* to resist further insertion of the surgical tool 120 into the insertion sheath 110. However, because the rollers are located on opposite sides of the surgical tool 120, they must rotate in opposite directions to generate the resistive force. Thus, the processor 352 may generate one actuator signal suitable to resist movement of the surgical tool 120 and transmit the actuator signal to actuator 140*a* but invert the actuator signal before transmit it to actuator 140*b*.

In a further embodiment, a surgeon may be performing an ablation procedure. During the procedure, the processor 352 may determine that too much tissue is being ablated and may generate an actuator signal to both resist movement of the trigger 212 on the power supply 210 as well as resist movement of the manipulandum 134 that controls movement of the surgical tool 130*a* performing the ablation. Such effects may provide an indication that further power should not be applied and that the distal tip of the tool should not be further moved towards the tissue being ablated. The processor 352 may generate one actuator signal suitable for both actuators and perform post-processing before transmitting the actuator signal, such as changing a magnitude, to each of the actuators 144, 240. After transmitting the actuator signal to the actuator, the method 500 returns to step 510 to receive another sensor signal or to step 520 to determine another status condition associated with the MIS procedure.

The method 500 shown in FIG. 5 is illustrative of one method according to some disclosed embodiments of the present invention and is not intended to limit the scope of the disclosure. Further, while the steps of the method 500 have been set forth in a particular order, there is no requirement that the steps be performed in such an order or that all of the steps shown in FIG. 5 be performed. For example, block 530 may be performed independently of whether a sensor signal is received, such as for actuator signals indicating a passage of time or other independent event. Further, a status condition need not be determined prior to generating an actuator signal or even at all.

While the methods and systems herein are described in terms of software executing on various machines, the methods and systems may also be implemented as specifically-configured hardware, such a field-programmable gate array (FPGA) specifically to execute the various methods. For example, referring again to FIGS. 1 and 2, embodiments can be implemented in digital electronic circuitry, or in computer hardware, firmware, software, or in combination of them. In one embodiment, a computer may comprise a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

Reference herein to "one embodiment" or "an embodiment" means that a particular feature, structure, operation, or other characteristic described in connection with the embodiment may be included in at least one implementation of the invention. The invention is not restricted to the particular embodiments described as such. The appearance of the phrase "in one embodiment" or "in an embodiment" in various places in the specification does not necessarily refer to the same embodiment. Any particular feature, structure, operation, or other characteristic described in this specification in relation to "one embodiment" may be combined with other features, structures, operations, or other characteristics described in respect of any other embodiment.

That which is claimed is:

1. A system comprising:
a surgical tool;
an insertion sheath configured to be partially inserted within a patient's body and to receive the surgical tool;
a first actuator coupled to the insertion sheath, the first actuator configured to receive a first actuator signal and, responsive to the first actuator signal, output a haptic effect to the insertion sheath;
a second actuator and a roller coupled to the insertion sheath, the roller configured to contact the surgical tool and to translate the surgical tool through the insertion sheath;
a sensor configured to be positioned externally in relation to the patient's body and to detect a physiological status of the patient, the sensor being separate from the surgical tool; and
a processor in communication with the first actuator, the second actuator, and the sensor, the processor configured to:
receive a sensor signal from the sensor, the sensor signal indicating a warning condition associated with the physiological status of the patient;
generate a second actuator signal based on the sensor signal; and
transmit the second actuator signal to the second actuator, the second actuator signal configured to cause the second actuator to rotate the roller to translate the surgical tool through the insertion sheath.

2. The system of claim 1, further comprising:
a second sensor coupled to a distal end of the surgical tool and configured to generate a second sensor signal.

3. The system of claim 2, wherein the processor is in communication with the second sensor and configured to:
receive the second sensor signal;
generate the second actuator signal based in part on the second sensor signal; and
transmit the second actuator signal to the second actuator.

4. The system of claim 2, wherein the second sensor is configured to detect a force.

5. The system of claim 4, wherein the second sensor signal comprises a sensed force associated with a contact force between the surgical tool and an obstacle, and wherein the second actuator is configured to output a force configured to maintain the contact force between a first threshold and a second threshold.

6. The system of claim 2, wherein the second sensor is configured to detect a fluid flow or a viscosity.

7. The system of claim 2, wherein the surgical tool comprises:
a handle configured to be manipulated;
a third actuator coupled to the handle, the third actuator configured to output a third haptic effect to the handle in response to a third actuator signal.

8. The system of claim 7, wherein the handle comprises a trigger and a fourth actuator, the fourth actuator configured to output a trigger haptic effect to the trigger.

9. The system of claim 7, wherein the handle and the third actuator are removably coupled to the surgical tool, the handle configured to be removed and discarded following a surgical procedure.

10. The system of claim 2, wherein the surgical tool comprises:
a therapeutic surgical tool; and
a power supply coupled to the therapeutic surgical tool, the power supply configured to control an intensity of a therapeutic effect provided by the therapeutic surgical tool, the power supply comprising:
a trigger, and
a third actuator coupled to the trigger, the third actuator configured to receive a third actuator signal and to output a trigger haptic effect to the trigger based on the third actuator signal.

11. The system of claim 10, wherein the trigger haptic effect comprises a vibration.

12. The system of claim 10, wherein the trigger haptic effect comprises a kinesthetic force configured to resist movement of the trigger.

13. The system of claim 1, wherein the sensor comprises a blood pressure monitor, an oxygen sensor, or a blood gas sensor.

14. The system of claim 7, wherein the third haptic effect comprises a vibration and is based at least in part on the second sensor signal.

15. The system of claim 1, wherein the second actuator and the roller are positioned within a subassembly that is releasably coupled to the insertion sheath, the subassembly configured to be removed from the insertion sheath following a surgical procedure.

16. The system of claim 1, wherein the first actuator comprises a piezoelectric actuator.

17. The system of claim 2, further comprising a third sensor directly positioned on the insertion sheath, wherein the processor is further configured to:
receive the second sensor signal from the second sensor, the second sensor signal indicative of a first parameter;
receive a third sensor signal from the third sensor, the third sensor signal indicative of a second parameter;
determine a difference between the first parameter and the second parameter; and
transmit the first actuator signal or the second actuator signal based on the difference between the first parameter and the second parameter.

18. The system of claim 17, wherein the first parameter comprises a first location of the surgical tool, the second parameter comprises a second location of the insertion sheath, and the difference comprises a distance between the first location and the second location.

19. The system of claim 1, wherein the processor is further configured to generate the first actuator signal, the first actuator signal indicating a passage of time.

20. The system of claim 1, further comprising:
a third actuator coupled to the surgical tool and configured to receive a third actuator signal and output a third haptic effect.

21. The system of claim 20, wherein the surgical tool is a first surgical tool that is configured to receive a second surgical tool, the system further comprising:
the second surgical tool, wherein the second surgical tool comprises a handle; and
a fourth actuator coupled to the handle of the second surgical tool and configured to receive a fourth actuator signal and output a fourth haptic effect to the handle.

22. The system of claim 21, wherein the handle comprises:
a trigger; and
a fifth actuator configured to output a fifth haptic effect to the trigger.

23. A system, comprising:
a surgical tool;
an insertion sheath configured to be partially inserted within a patient's body, the insertion sheath configured to receive the surgical tool;
a non-contact inductive actuator having a cylindrical shape, the inductive actuator coupled to the insertion sheath and configured to allow the surgical tool to pass through the inductive actuator and to translate the surgical tool through the insertion sheath;
a sensor configured to be positioned externally in relation to the patient's body and to detect a physiological status of the patient, the sensor being separate from the surgical tool; and
a processor in communication with the non-contact inductive actuator and the sensor, the processor configured to:
receive a sensor signal from the sensor, the sensor signal indicating a warning condition associated with the physiological status of the patient;
generate an actuator signal based on the sensor signal; and
transmit the actuator signal to the inductive actuator, the actuator signal configured to cause the inductive actuator to translate the surgical tool through the insertion sheath via electromagnetic induction forces.

24. The system of claim 23, wherein the inductive actuator is configured to translationally assist or resist movement of the surgical tool though the insertion sheath.

* * * * *